(12) United States Patent
Bonner et al.

(10) Patent No.: US 8,719,058 B2
(45) Date of Patent: May 6, 2014

(54) OUTCOMES BASED SERVICE PROVIDER NETWORKS

(75) Inventors: Robert E. Bonner, Hartford, CT (US);
Joseph D. Pagano, Wallingford, CT (US); William J. Bohn, West Hartford, CT (US)

(73) Assignee: Hartford Fire Insurance Company, Hartford, CT (US)

( * ) Notice: Subject to any disclaimer, the term of this patent is extended or adjusted under 35 U.S.C. 154(b) by 45 days.

(21) Appl. No.: 12/958,704

(22) Filed: Dec. 2, 2010

(65) Prior Publication Data

US 2012/0143629 A1    Jun. 7, 2012

(51) Int. Cl.
*G06Q 40/08* (2012.01)

(52) U.S. Cl.
USPC .................................................. 705/4

(58) Field of Classification Search
CPC ..................................................... G06Q 40/08
USPC .................................................. 705/4
See application file for complete search history.

(56) References Cited

U.S. PATENT DOCUMENTS

| | | | | |
|---|---|---|---|---|
| 6,192,347 | B1 * | 2/2001 | Graff | 705/36 R |
| 6,324,516 | B1 * | 11/2001 | Shults et al. | 705/2 |
| 7,107,239 | B2 * | 9/2006 | Graff | 705/36 R |
| 2002/0046144 | A1 * | 4/2002 | Graff | 705/36 |
| 2004/0267595 | A1 * | 12/2004 | Woodings et al. | 705/9 |
| 2005/0080653 | A1 * | 4/2005 | Stemple | 705/4 |
| 2006/0106774 | A1 * | 5/2006 | Cohen et al. | 707/3 |
| 2006/0116914 | A1 * | 6/2006 | Stemple | 705/4 |
| 2011/0077977 | A1 * | 3/2011 | Collins et al. | 705/4 |
| 2011/0119077 | A1 * | 5/2011 | Gice et al. | 705/2 |
| 2011/0288879 | A1 * | 11/2011 | Gice et al. | 705/2 |

OTHER PUBLICATIONS

"A Guide to High-Value Physician Services in Workers' Compensation—How to find the best available care for your injured workers", American College of Occupational and Environmental Medicine, IAIABC, 2010, 11 pages.

Ann Lawthers, et al, "Measuring Quality in Workers' Compensation Managed Care Organizations: Technical Manual of Performance Measures", Mar. 2000, 179 pages.

(Continued)

*Primary Examiner* — Lindsay M. Maguire
(74) *Attorney, Agent, or Firm* — Volpe and Koenig, P.C.

(57) ABSTRACT

A system and method are provided for determining a composition of a service provider network for providing services according to a workers' compensation insurance plan. The system and method acquires claim information, which describes workers' compensation claims and medical service providers, and determines a metric value for each of the medical service providers, adjusts the metric values, assigns scores based on the adjusted metric values, determines an average of the assigned scores, and generates results data based on the assigned scores. The results data indicates, for each of the medical service providers, whether the medical service provider should be included in the service provider network. The service provider metrics include a metric that relates to an amount paid per claim and a percentage of claims that involved lost time.

30 Claims, 6 Drawing Sheets

(56) References Cited

OTHER PUBLICATIONS

David Huth, "Time PPOs Went the Way of the Dodo?", Risk and Insurance Online-Story; http://www.riskandinsurance/printstory.jsp?storyID+218226535, Jun. 5, 2009, pp. 1-2.

"News and information for LWCC OMNET providers"; Proviso, vol. 10, Issue 1, Dec. 2008, 6 pages.

Roberto Ceniceros, "Employers work with physicians to cut workers comp costs", Business Insurance, http://www.businessinsurance.com/article/20090823/ISSUE03/308239972, Aug. 23, 2009, pp. 1-3.

"A Guide to High-Value Physician Services in Workers' Compensation—How to find the best available care for your injured workers", American College of Occupational and Environmental Medicine, IAIABC, 2010, pp. 1-11.

Joseph Pagano, "Improving Claim Outcomes through Provider Performance Measures", Industry Update, Risk Management Innovation from SRS, Specialty Risk Services, LLC, 2010, 2 pages.

* cited by examiner

Service Provider Network Composition Results

| Service Provider Name | Final Score | In Network? | Average Claimant Satisfaction | Average Claimant Satisfaction Score | Average Disability Days | Average Disability Days Score | Average Paid Loss | Average Paid Loss Score |
|---|---|---|---|---|---|---|---|---|
| Provider One | 1 | Y | 6 | 1 | 12 | 0 | $16,000 | 3 |
| Provider Two | 5 | N | 0 | 5 | 130 | 5 | $50,000 | 5 |
| Provider Three | 0.666 | Y | 8 | 0 | 11 | 0 | $3,000 | 1 |

OUTCOMES BASED SERVICE PROVIDER NETWORKS

TECHNICAL FIELD

The subject matter disclosed herein relates to computer systems, and particularly to the storage, processing, and display of data related to service provider networks.

BACKGROUND

Workers' compensation insurance is an insurance that provides benefits to workers that are injured in the course of their employment. Benefits that may be provided as part of workers' compensation include disability benefits, rehabilitation services, and medical care. An employer may purchase a workers' compensation insurance policy from an insurance provider. The policy may identify a network of service providers that treat the employees of the employer according to the policy. Service providers may include hospitals, doctors, and rehabilitation providers that administer care to injured workers.

Service providers may vary in terms of the quality of care that they provide to injured workers. For example, a service provider may provide superior medical treatment versus other service providers, and workers that receive care from the superior service provider may consistently have better outcomes (i.e., may recover from injuries more quickly) than workers who are treated by other service providers.

To provide the best care possible to injured workers, insurance providers and employers want the best possible service providers to be included in their service provider networks. However, it may be difficult for insurance providers and employers to determine who the best service providers are. Therefore, new technologies are required that may be used to assess the effectiveness of service providers, such that the best possible care may be provided to injured workers.

SUMMARY

Disclosed herein are technologies that may be used to determine the composition of service provider networks. Service providers may be compared based on a number of metrics related to the services they provide. As an example, medical service providers may be compared based on factors such as how quickly patients in their care recover from injuries, and how satisfied patients are with the care they receive. A service provider network may be defined as including only service providers with metrics that meet a given threshold. In the context of workers' compensation insurance, the disclosed technologies may be used to direct injured workers to medical service providers that provide superior care, thereby achieving better outcomes for injured workers.

A system for determining a composition of a service provider network for providing services according to a workers' compensation insurance plan may include a computer-readable storage medium, at least one processor, and a display device. The computer-readable storage medium may store claim information. The claim information may describe workers' compensation claims and the medical service providers that provided medical services related to the workers' compensation claims. The at least one processor may determine, for each of the medical service providers, a metric value for each of a number of service provider metrics. This may be based on the claim information, and/or other factors. The service provider metrics may include a metric that relates to an amount paid per claim or a percentage of claims that involved lost time. The at least one processor may adjust the metric values based on one or more metric values. Further, the at least one processor may assign scores to each of the medical service providers based on the adjusted metric values, and may determine averages for the assigned scores for each of the medical service providers. Further, the at least one processor may generate results data based on the determined averages of the assigned scores. The results data may indicate, for each of the medical service providers, whether the medical service provider is included in the service provider network. The display device may display the results data.

A computer-implemented method for determining a composition of a service provider network may include a computer-readable storage storing claim information. The claim information may describe workers' compensation claims and the medical service providers that provided medical services related to the workers' compensation claims. At least one processor may determine, for each of the medical service providers, a metric value for each of a number of service provider metrics. This may be based on the claim information, and/or other factors. The service provider metrics may include a metric that relates to an amount paid per claim or a percentage of claims that involved lost time. The at least one processor may adjust the metric values based on one or more metric values, may assign scores to each of the medical service providers based on the adjusted metric values, and may determine averages for the assigned scores for each of the medical service providers. Further, the at least one processor may generate results data based on the determined averages of the assigned scores. The results data may indicate, for each of the medical service providers, whether the medical service provider is included in the service provider network. The results data may then be displayed by a display device.

A computer-readable medium may store processor-executable instructions which, when executed by at least one processor, will cause the at least one processor to perform a method for determining a composition of a service provider network. The method may include the at least one processor receiving claim information. The claim information may describe workers' compensation claims and the medical service providers that provided medical services related to the workers' compensation claims. The at least one processor may determine, for each of the medical service providers, a metric value for each of a number of service provider metrics. This may be based on the claim information, and/or other factors. The service provider metrics may include a metric that relates to an amount paid per claim or a percentage of claims that involved lost time. The at least one processor may adjust the metric values based on one or more metric values, may assign scores to each of the medical service providers based on the adjusted metric values, and may determine averages for the assigned scores for each of the medical service providers. Further, the at least one processor may generate results data based on the determined averages of the assigned scores. The results data may indicate, for each of the medical service providers, whether the medical service provider is included in the service provider network. The at least one processor may then display the results data via a display device.

BRIEF DESCRIPTION OF THE DRAWINGS

A more detailed understanding may be had from the following description, given by way of example in conjunction with the accompanying drawings wherein.

DETAILED DESCRIPTION

Figure 1:
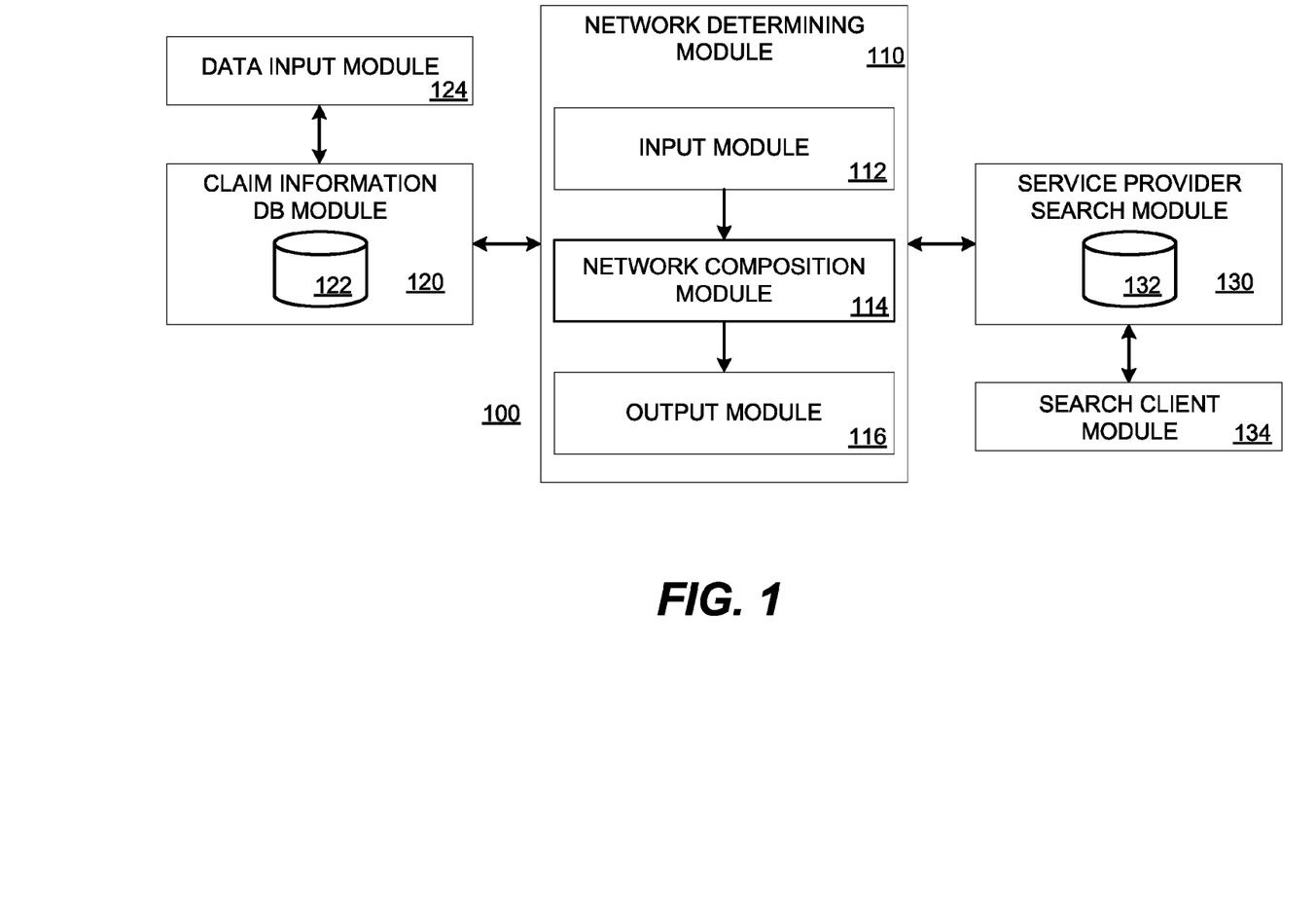
FIG. 1 shows an example architecture 100 for determining the composition of a service provider network.

FIG. 1 shows an example architecture 100 for determining the composition of a service provider network for use in the context of workers' compensation insurance. As will be describe in further detail below, the example architecture 100 of FIG. 1 may be used to determine if specific service providers should be included in a service provider network, and/or to determine how service providers within a network should be ranked or classified.

The example architecture 100 includes a network determining module 110, which is configured to analyze data and determine the composition of a service provider network. The example architecture 100 may also includes a claim information database 122, claim information database module 120, and a data input module 124, which perform functionality related to the storage of data that describes services that have been provided to users by service providers. Further, the example architecture 100 may include a service provider search module 130, service provider network database 132, and a search client module 134, which together provide data to users about medical services providers from which the users may receive services.

The claim information database 122 may be stored on one or any number of computer-readable storage media (not depicted). The claim information database 122 may be or include, for example, a relational database, a hierarchical database, an object-oriented database, one or more flat files, one or more spreadsheets, and/or one or more structured files. The claim information database 122 may store information related to claims that have been filed and medical service providers that have provided services related to the claims. The claim information database 112 may include data related to service providers who are already included in one or more service provider networks, service providers who are not currently in a service provider network, and/or any combination thereof. For each claim, the claim information database 122 may include one or more parameters associated with the claim, such as: the amount paid by the insurance provider for the claim; the number of disability days for which the claimant missed work; whether the claim is associated with litigation or other legal activity; the number of days the claim has stayed open, which may also be referred to as the "age" or "maturity" of a claim; whether the claim settled; whether the compensability of the claim has been determined (in other words, whether a determination has been that the claim relates to an injury that should be compensated by workers' compensation insurance, or whether investigation into this topic is still ongoing); the number of service provider office visits associated with the claim; whether surgery was associated with the claim; whether inpatient hospitalization was associated with the claim; the age of the claimant; a treatment delay time (i.e., the period of time that passed between the injury and when the claimant first sought treatment for the injury); a location where the injury and/or the treatment took place; a service provider that provided services associated with the claim; and/or other information. Further, the claim information database 122 may include information such as whether each claim involved lost time. Many jurisdictions define a waiting period that follows the onset of an injury. Work that is missed during this waiting period does not constitute lost time; however, work that is missed by an injured working after the waiting period is considered lost time. Alternatively or additionally, the claim information database 122 may store qualitative information related to the claims, such as: data that describes the satisfaction of the claimant with the care received; data that describes the satisfaction of a claims adjuster that handled the treatment associated with the claim with the service provider; and/or information that describes the satisfaction of the claimant's employer with how the service provider handled the treatment associated with the claim. A level of satisfaction may be represented using a numeric scale, with different values along the scale corresponding to different levels of satisfaction. As an example, a scale of zero to ten may be used, wherein zero represents the lowest level of satisfaction and ten represents the highest level of satisfaction).

The claim information database module 120 may perform functionality such as adding data to, modifying data in, querying data from, and/or retrieving data from the claim information database 122. The claim information database module 120 may be, for example, a database management system (DBMS), a database driver, a module that perform file input/output operations, and/or other type of module. The claim information database module 120 may be based on a technology such as Microsoft SQL Server, Microsoft Access, MySQL, PostgreSQL, Oracle Relational Database Management System (RDBMS), Microsoft Excel, a NoSQL database technology, and/or any other appropriate technology.

The data input module 124 may perform functionality such as providing data to the claim information database module 120 for storage in the claim information database 122. The data input module 124 may be, for example, a spreadsheet program, a database client application, a web browser, and/or any other type of application that may be used to provide data to the claim information database module 120.

The network determining module 110 may perform functionality such as determining the composition of a service provider network based on information stored in the claim information database 122. The network determining module 110 may include an input module 112, a network composition module 114, and an output module 116. The input module 112 may perform functionality such as obtaining data from the claim information database module 120 and providing the data to the network composition module 144. The network composition module 114 may perform functionality such as analyzing the data provided by the input module 112 to determine the composition of the service provider network. This may include, for example, analyzing how well service providers perform in a number of parameters (such as those described above as stored in the claim information database 122), assigning scores to the service providers based on their performances, and ranking service providers based on their scores. The network composition module 114 may determine whether service providers should be included in a service provider network or not, based on the scores. Alternatively or additionally, the network composition module 114 may determine that service providers within a certain range of scores may be classified differently from service providers within other ranges. For example, service providers with scores above a threshold value should be classified as "preferred" providers within the network, while providers with lower scores may not.

The output module 116 may obtain results determined by the network composition module 114 and may output the results in a number of ways. For example, the output module 116 may store the results in one or more computer-readable media (not depicted), and/or may send information related to the results to an output device (not depicted) such as a printer, display device, or network interface. Alternatively or additionally, the output module 116 may transmit and/or otherwise output its results for storage in the service provider network database 132. Further details regarding functionality that may be performed by the network determining module 110 are provided below with reference to FIG. 2.

The service provider network database 132 may store information that describes the composition of a service provider network. For example, the service provider network database 132 may include information that identifies service providers in the network, and may include contact information, specialty information, geographic information, information regarding how well service providers have been ranked by the network composition module 114 (for example, whether providers are "preferred" or not), and/or information associated with the service providers. The service provider network database 132 may be stored on one or any number of computer-readable storage media (not depicted). The claim information database 122 may be or include, for example, a relational database, a hierarchical database, an object-oriented database, one or more flat files, one or more spreadsheets, and/or one or more structured files.

The service provider search module 130 may provide search functionality that allows users to search for service providers whose information is stored in the service provider network database 132. A user may interact with the service provider search module 130 using the search client module 134. The search client module 134 may provide a user interface that the user may use to enter information to search for a service provider. As an example, the search client module 134 may be a web browser or similar application.

As an example, a user may wish to search for a medical service provider for a particular medical specialty that is geographically nearby to the user's location. The user may enter these search parameters into the user provided by the search client module 134, which may transmit the search parameters to the service provider search module 130. The search parameters may include, for example, an area of specialization, name, geographic location (such as a state, city, and/or zip code), and/or other parameters. The service provider search module 130 may then search for a service provider in the service provider database 132 that matches the parameters, and transmit search response information to the search client module 134. The service provider search module 130 may generate the results based on information such as how the service providers have been ranked by the network composition module 114. For example, the service provider search module 130 may generate results that will display preferred providers before providers with less favorable rankings are displayed. Alternatively or additionally, the service provider search module 130 may generate the search results to include only service providers within a certain range of scores. The search client module 134 may then display the search response information to the user via a display device (not depicted). The search response information may include contact information such as telephone numbers, addresses, and/or other information related to the medical service providers that match the search criteria. Using the contact information, the user may contact the service providers and initiate a visit to the service provider to begin medical treatment.

Each or any combination of the modules 110, 112, 114, 116, 124, 120, 130, 134 may be implemented as software modules, specific-purpose processor elements, or as combinations thereof. A suitable software module may be or include, by way of example, one or more executable programs, one or more functions, one or more method calls, one or more procedures, one or more routines or sub-routines, one or more processor-executable instructions, and/or one or more objects or other data structures.

The example architecture 100 of FIG. 1 may be used in any number of different contexts. As one example, an insurance provider may control the data input module 124, claim information database module 120, claim information database 122, and network determining module 110. The insurance provider may use these modules 110, 120, 124 to determine the composition of a service provider network for use with a workers' compensation policy. The insurance provider may provide the composition of the service provider network to a third party search vendor, which may control the service provider search module 130. The insurance provider may provide the workers' compensation policy to an employer. When employees of the employer are injured, the employees may search for medical service providers using the search client module 134, thereby interacting with the service provider search module 130.

As an additional example, a third party administrator (TPA) of a self-funded workers' compensation plan may control the data input module 124, claim information database module 120, claim information database 122, and network determining module 110. The TPA may use these modules 110, 120, 124 to determine the composition of a service provider network for use with the self-funded plan. The TPA and/or a third party search vendor may control the service provider search module 130.

Further, an insurance provider or TPA may interact with service providers differently based on the results generated by the network determining module 110. For example, in an instance where the network determining module 110 classifies service providers, an insurance provider or TPA may perform claim management differently with service providers that are in the different classifications. For example, an insurance provider or TPA may reduce or completely remove claim management for service providers with favorable scores, while focusing additional energy and resources for claim management for providers with less favorable scores.

Figure 2:
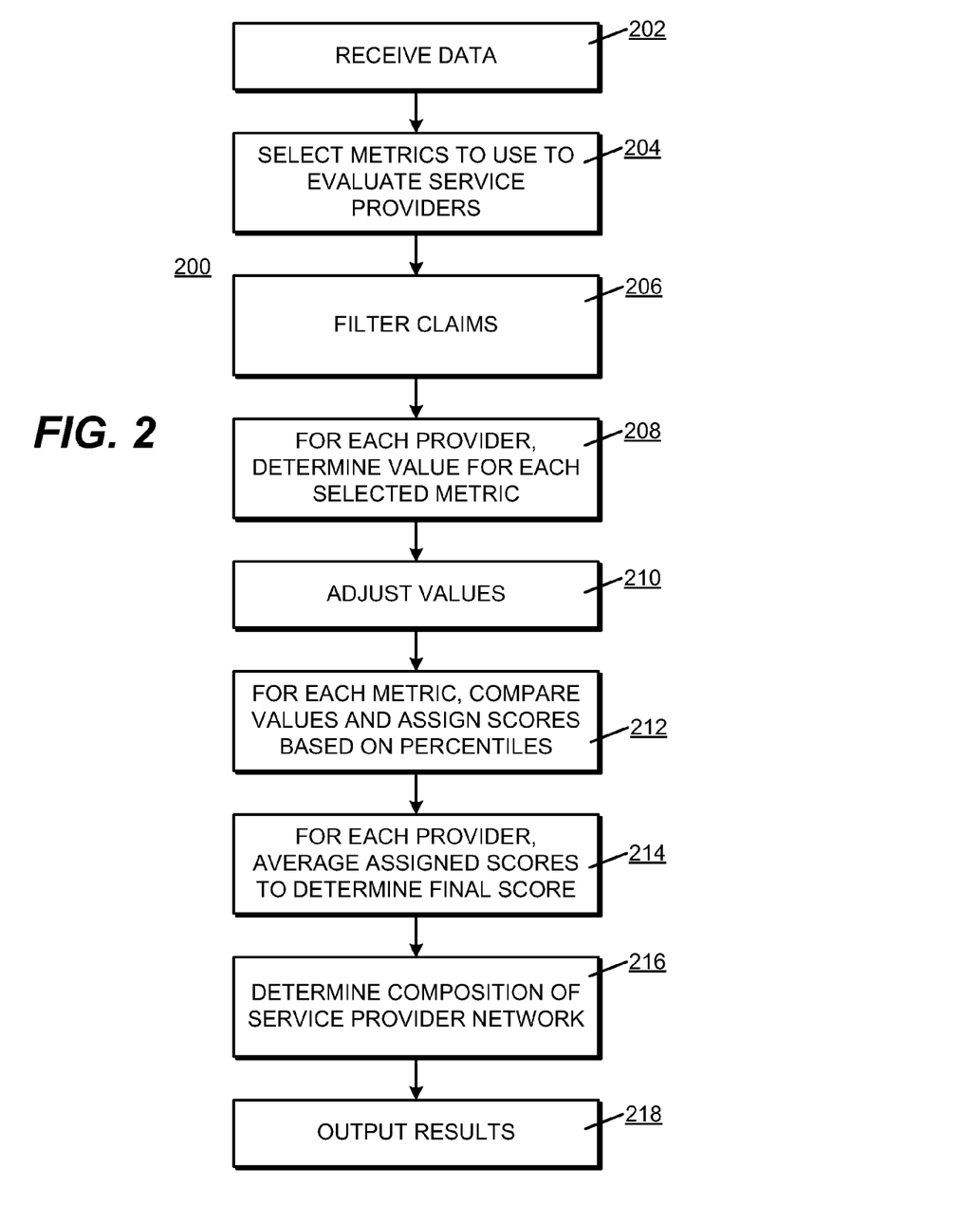
FIG. 2 shows an example method for determining the composition of a service provider network.

FIG. 2 shows an example method 200 for determining the composition of a service provider network. The method 200 may begin with receiving data related to service providers and claims associated with services provided by the service providers (step 202). This may include, for example, reading the data from a computer-readable storage medium and/or receiving the data via a network interface. The data may be or include the information described above with reference to FIG. 1 as stored in the claim information database 122.

Next, metrics for evaluating service providers may be selected (step 204). The metrics may include, for example, an average number of disability days experienced by workers that were treated by a service provider, or a percentage of claims that involved lost time. As further examples, the metrics may include: an average paid loss per claim; a percentage of claims that are associated with legal and/or litigation activity; an average claim duration; a percentage of claims that are open after twelve months; a percentage of claims for which compensability has not yet been determined; a percentage of claims that were settled; an average number of provider office visits for claims; a percentage of claims that involve surgery; a percentage of claims that involve inpatient hospitalization; an average number of lost work days per claim; average levels of satisfaction with provided services, as indicated by claimants, claims adjusters, and/or employers; and/or other metrics. While a number of example metrics are described above in terms of averages, the metrics may also include metrics that are based on other statistical functions such as means, modes, correlations, regressions, or standard deviations.

Claims may then be filtered, based on a number of different parameters. (step 206). This may include removing data related to claims that have parameters that are far above or below the average for that parameter. For example, claims related to catastrophic injuries may have much higher associated costs, disability days, and/or higher values for other parameters, and data associated with these claims may be removed. As one example, claims that involved payment of more than a given threshold for a given type of expense within a given period of time may be removed. For example, claims that involved payment of more than $150,000 in medical expenses within the first six months of the filing of the claim may be removed. Alternatively or additionally, claims that involved a low total payment may be removed. For example, claims that involved a total payment of less than $50,000 may be filtered out of the received data. Alternatively or additionally, filtering may include removing data that is outside of a particular geographic area of interest. For example, if a particular zip code, state, or other geographic area is the region of interest, then claims that do not pertain to the geographic area may be removed.

Then, for each metric, values may be determined for each of the service providers, based on the received data (step 208). This may include averaging and/or determining percentages for the data from the received data that is associated with claims handled by the service providers. For example, if a selected metric is an average satisfaction level for claimants, then the claimant satisfaction level values will be averaged for each service provider. Corresponding processing may be performed for each of the selected metrics.

The metric values may then be adjusted to obtain metric values that are consistent values across service providers (step 210). Adjusting the metric values may include scaling and/or otherwise modifying the metric values, and may be based on a number of different factors. For example, metric values may be adjusted based on one or more adjustment parameters, such as the types of injuries a service provider has treated, the ages of claimants handled by a service provider, and/or the ages of claims handled by a service provider.

To adjust metric values based on the type of injuries a service provider has treated (step 210), the following approach may be employed. First, claims may be grouped according to the type of injury (also referred to as the "Major Diagnostic Category (MDC)") of the injury. Then, for each MDC, an average metric value for claims associated with that MDC may be determined. Then, the average metric values for each MDC may be compared, and values ("scaling factors") may be determined for each of the MDCs. Scaling factors are values that may be used to multiply the average metric values to bring the average metric values onto a common scale. Finally, metric values may be multiplied by the scaling factors to obtain adjusted metric values.

The following is an example of how metric values may be adjusted based on MDCs: A set of claims may relate to three example MDCs, "Injury One," "Injury Two," and "Injury Three." The average paid loss for all claims for Injury One may be $5,000; the average paid loss for all claims for Injury Two may be $10,000; and the average paid loss for all claims for Injury Three may be $20,000. According to this example, the average paid loss is two times greater for Injury Three than for Injury Two, and four times greater for Injury Three than for Injury One. Therefore, all paid loss values for claims that are associated with Injury One may be adjusted by being multiplied by a scaling factor of four, and all paid loss values for claims that are associated with Injury Two may be adjusted by being multiplied by a scaling factor of two. By multiplying these paid loss values with these scaling factors, the average paid loss across all three of the MDCs will be the same and paid loss values across the different DMCs may be compared on a normalized scale.

To adjust metric values based on the ages of claimants handled by a service provider (step 210), the following approach may be employed. Claims may be grouped according to the age of the claimants. Then, for each group, an average metric value for claims associated with the age may be determined. Then, a function may be derived from the averages. The function may take a claimant age range as an input, and generate a corresponding average metric value (such as, for example, an average number of disability days) as an output. Metric values may then be compared against values generated by the function, and be adjusted based on the difference between the metric values and the corresponding values generated by the function.

Figure 3:
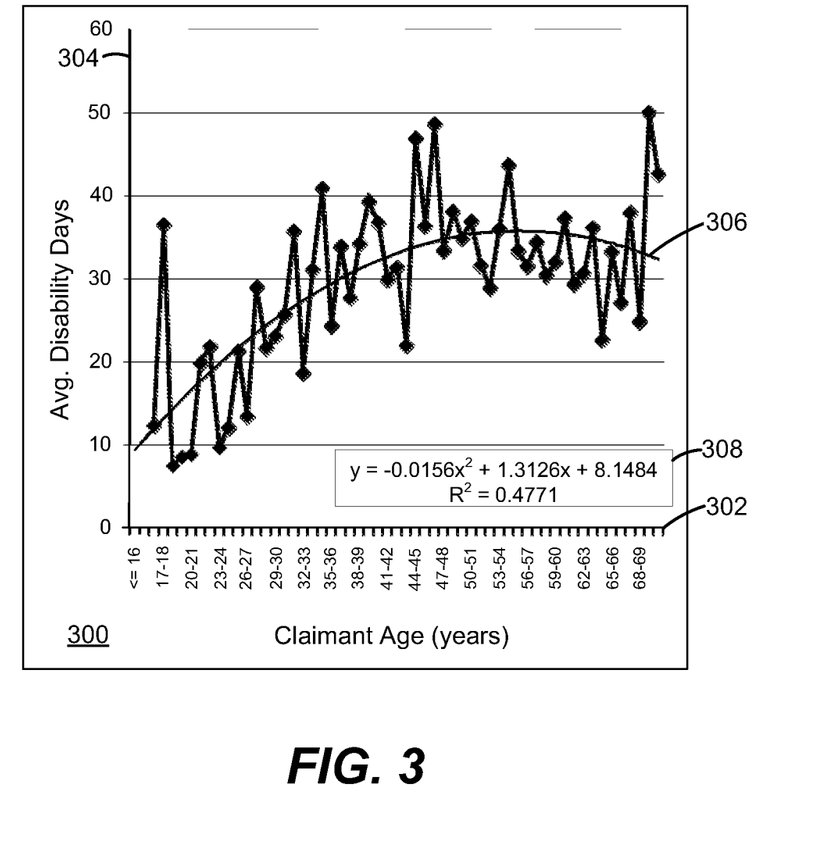
FIG. 3 shows an example graph that shows a function that may be used for normalizing data in the context of determining the composition of a service provider network.

Referring now to both FIG. 2 and FIG. 3, FIG. 3 shows an example graph 300 that shows an example function 308 that may be used to adjust metric values based on the ages of claimants handled by a service provider (step 210). The graph 300 includes an X axis 302, which corresponds to claimant ages, and a Y axis 304, which corresponds to an average number of disability days. The graph 300 also includes a curve 306, which is a graphical representation of the function 308. The curve 306, as shown in FIG. 3, shows correspondences between claimant age ranges (on the X axis 302) and average disability days (on the Y axis 304).

Referring again to FIG. 2, to adjust metric values based on the ages of claims handled by a service provider (step 210), the following approach may be employed. Claims may be grouped according to the age (in months, or some other unit of time) of the claim. Then, for each group, an average metric value for claims associated with the age. Then, a function may be derived from the averages. The function may take a claim age as an input, and generate a corresponding average metric value (such as, for example, an average disability days) as an output. Metric values may then be compared against values generated by the function, and be adjusted based on the difference between the metric values and the corresponding values generated by the function.

Figure 4:
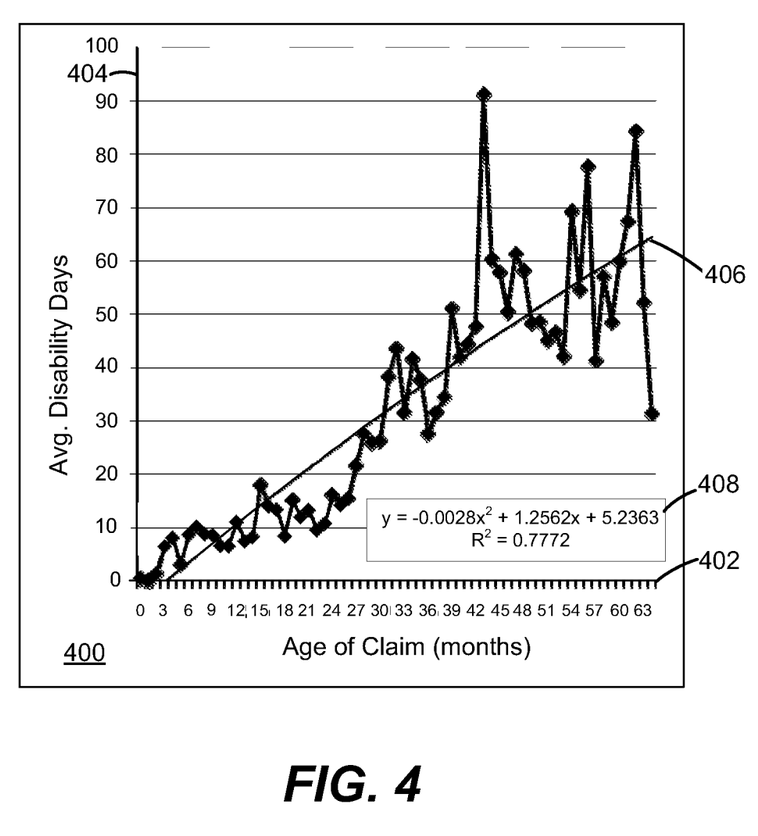
FIG. 4 shows a second example graph that may be used for normalizing data in the context of determining the composition of a service provider network.

Referring now to both FIG. 2 and FIG. 4, FIG. 4 shows an example graph 400 that shows an example function 408 that may be used to adjust metric values based on the ages of claims handled by a service provider (step 210). The graph 400 includes an X axis 402, which corresponds to claim age ranges, and a Y axis 404, which corresponds to an average number of disability days. The graph 400 also includes a curve 406, which is a graphical representation of the function 408. The curve 406, as shown in FIG. 4, shows correspondences between claim age ranges (on the X axis 402) and average disability days (on the Y axis 404).

Referring again to FIG. 2, after the metric values are adjusted (step 210), the adjusted metric values may be compared, and scores may be assigned to service providers based on the comparisons (step 212). Here, adjusted metric values for each metric may be sorted into ascending or descending order, and percentage range distributions for the sorted values may be determined.

The following table (Table 1) shows examples of percentage range distributions for a number of example metrics:

TABLE 1

|  | Top 10% | Top 25% | Top 50% | Top 75% | Top 90% |
|---|---|---|---|---|---|
| Average claimant satisfaction | 7 | 5 | 3 | 2 | 1 |
| Average disability days | 14 | 30 | 55 | 90 | 115 |
| Average paid loss | $2,000 | $5,000 | $15,000 | $30,000 | $40,000 |

In the example of Table 1, the metrics that are used are average claimant satisfaction, average disability days, and average paid loss. For average claimant satisfaction, values may be defined according to a scale of zero to ten, wherein zero represents the lowest level of satisfaction and ten represents the highest level of satisfaction. Table 1 is organized such that percentage ranges for qualitatively better values are on the left size of the table (e.g., a higher claimant satisfaction value is considered better than a lower claimant satisfaction value), while percentage ranges for qualitatively lesser values are on the right side of the table.

Table 1 shows border values for the different percentage ranges for each of the average claimant satisfaction, average disability days, and average paid loss metrics. According to the example of Table 1, the top 10% of claimant satisfaction values were at seven or above; the next 15% of claimant satisfaction values were from five to six; the next 25% of values were from three to four; the next 25% of values were from one to two; and the next 15% of values were one. Similarly, the top 10% of values for the average number of disability days were less than fourteen; in the next percentage ranges for this metric, the average numbers of disability days were less than 30, 55, 90, and 155, respectively. Further, the top 10% of values for average paid loss were less than $2,000; in the next percentage ranges for this metric, the values for average paid loss were less than $5,000, $15,000, $30,000, and $40,000, respectively. After percentage range distributions are determined, each service provider may be assigned a score for each metric, based on which percentage range the service provider falls within for that metric. The following table (Table 2) shows example values that may be assigned based on percentage distributions:

TABLE 2

| Percentage Range for Metric | Value to be Assigned |
|---|---|
| Top 90%-100% | 5 |
| 75%-90% | 4 |
| 50%-75% | 3 |
| 25%-50% | 2 |
| 10%-25% | 1 |
| 0%-10% | 0 |

As a further example that uses the examples of Table 1 and Table 2, a service provider may have the following values: an average claimant satisfaction value of seven; an average disability days value of fifty; and an average paid loss value of $35,000. For average claimant satisfaction, this service provider would fall within the top 90%-100% range, and so would be assigned a value of five; for average disability days, this service provider would fall within the 50%-75% range, and so would be assigned a value of three; and for average paid loss, this service provider would fall within the 10%-25% range, and so would be assigned a value of two. In summary, the service provider would be assigned the following scores: {5, 3, 1}.

As shown in the above example, favorable percentage ranges correspond to higher values (e.g., the top 90%-100% range is associated with a value of five, the 75%-90% range is associated with a value of four, and so on.) In a variation on the above example, favorable percentage ranges may correspond to lower values and less favorable percentage ranges may correspond to higher values. According to this variation, the top 90%-100% range may correspond to a value of zero, the 75%-90% range may correspond to a value of one, the 50%-75% range may correspond to a value of three, and so on.

Final scores for each service provider may then be determined by averaging the metric scores assigned to each service provider (step 214). Referring again to the above example, the service provider was assigned the following scores: {5, 3, 1}. Averaging these scores would result in a final score for the service provider of three. Alternatively or additionally, the final scores may be a weighted average.

Then, the composition of the service provider network may be determined based on the final service provider scores (step 216). This may include, for example, determining that service providers with a final score below a threshold are not included in the service provider network, and that service providers with a final score above the threshold are included in the service provider network. As one example, a value of three may be used for the threshold; according to this example, service providers with a final score of three or above may be included in the service provider network, while those with a final score of one or two are not included in the service provider network. Alternatively or additionally, service providers within a certain range of scores may be classified differently from service providers within other ranges. For example, service providers with a final score above a threshold value may be considered to be "preferred" providers within the network, while providers with final scores below the threshold may be considered part of the network, but may not be designated with a preferred status. In a variation on the above, lower final scores may be considered better than higher local scores; in such an instance, determining the composition of the service provider network may include, as an example, determining that service providers with a final score above a threshold are not included in the service provider network and that service providers with a final score below the threshold are included in the service provider network.

Once the composition of the service provider network is determined, the composition and/or other related information may then be output (step 218). This may include, for example, storing the results in one or more computer-readable media, displaying the results on a display device, printing the results via a printer, and/or communicating the results via a network interface. The other related information that may also be output may include any of the data or other parameter described above as used during steps 202 through 216, and/or other parameters.

Figure 5:
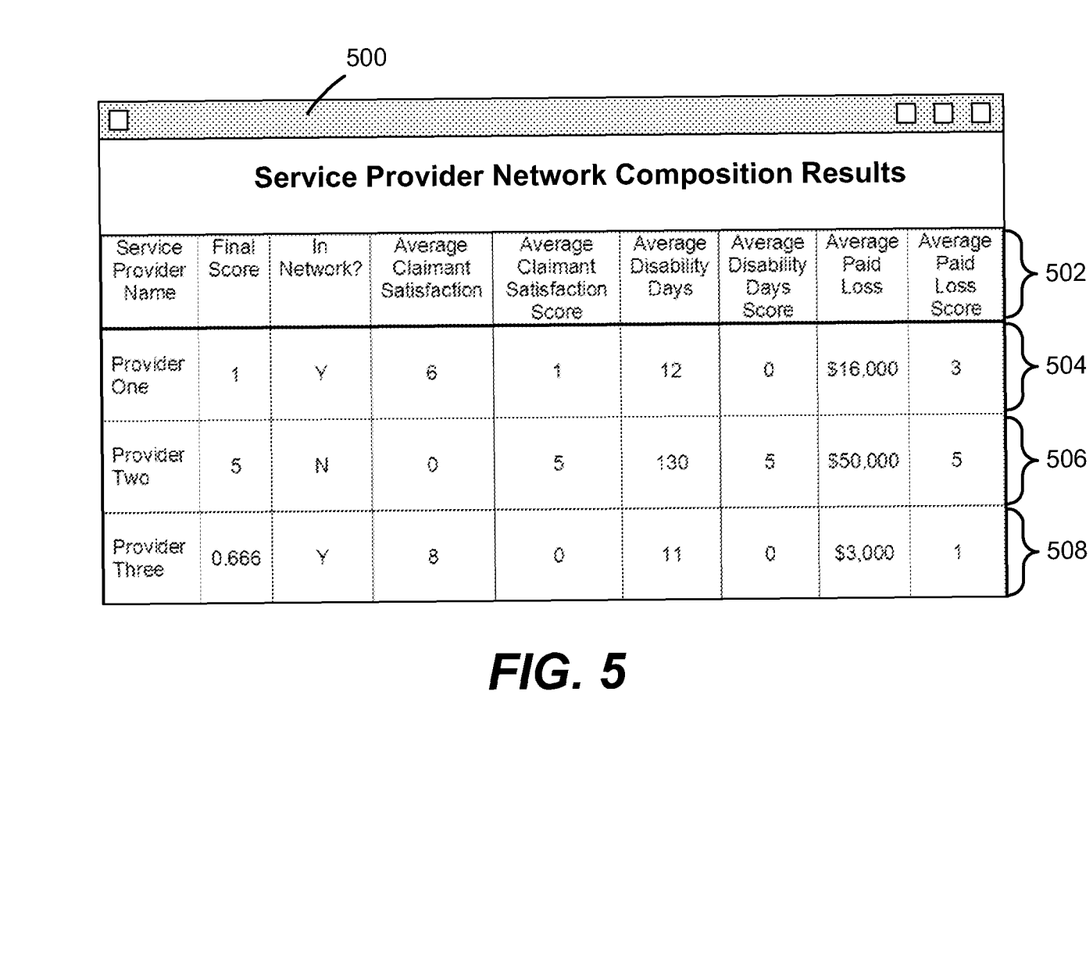
FIG. 5 shows an example user interface element that that may be used to display data that describes the composition of a service provider network.

Referring now to both FIG. 2 and FIG. 5, FIG. 5 shows an example user interface element 500 that may be used to display data that describes the composition of an example service provider network on a display device (step 218). The example user interface element 500 includes a header row area 502, a first row area 504, a second row area 506, and a third row area 508.

The user interface element 500 of FIG. 5 shows service provider network composition data that relates to three example service providers, Provider One, Provider Two, and Provider Three. The first row area 504 shows data that relates to Provider One; Provider One has an average claimant satisfaction score of one, an average disability days score of zero, and an average paid loss score of three. These scores may be determined using the example parameters described above with reference to Table 1 and Table 2. These scores, when averaged, result in the final score of one, as shown in the first row area 504. The second row area 506 and the third row area 508 show corresponding data for Provider Two and Provider Three, respectively. In this example, a threshold final value of three may have been used to determine whether a service provider should be included in the service provider network or not. According to this example, and as shown in the row areas 502, 504, 506 in the user interface element 500, Provider One and Provider Three are included in the service provider network, while Provider Two is not included in the service provider network.

Referring to both FIG. 1 and FIG. 2, the method 200 of FIG. 2 may be performed using the example architecture 100 of FIG. 1, or any other appropriate architecture. For example, the network determining module 110 of FIG. 1 may perform the method 200 of FIG. 2. Alternatively or additionally, the input module 112 of FIG. 1 may perform step 202 of the method 200 of FIG. 2, the network composition module 114 of FIG. 1 may perform steps 204 through 216 of the method 200 of FIG. 2, and the output module 116 of FIG. 1 may perform step 218 of the method 200 of FIG. 2.

Figure 6:
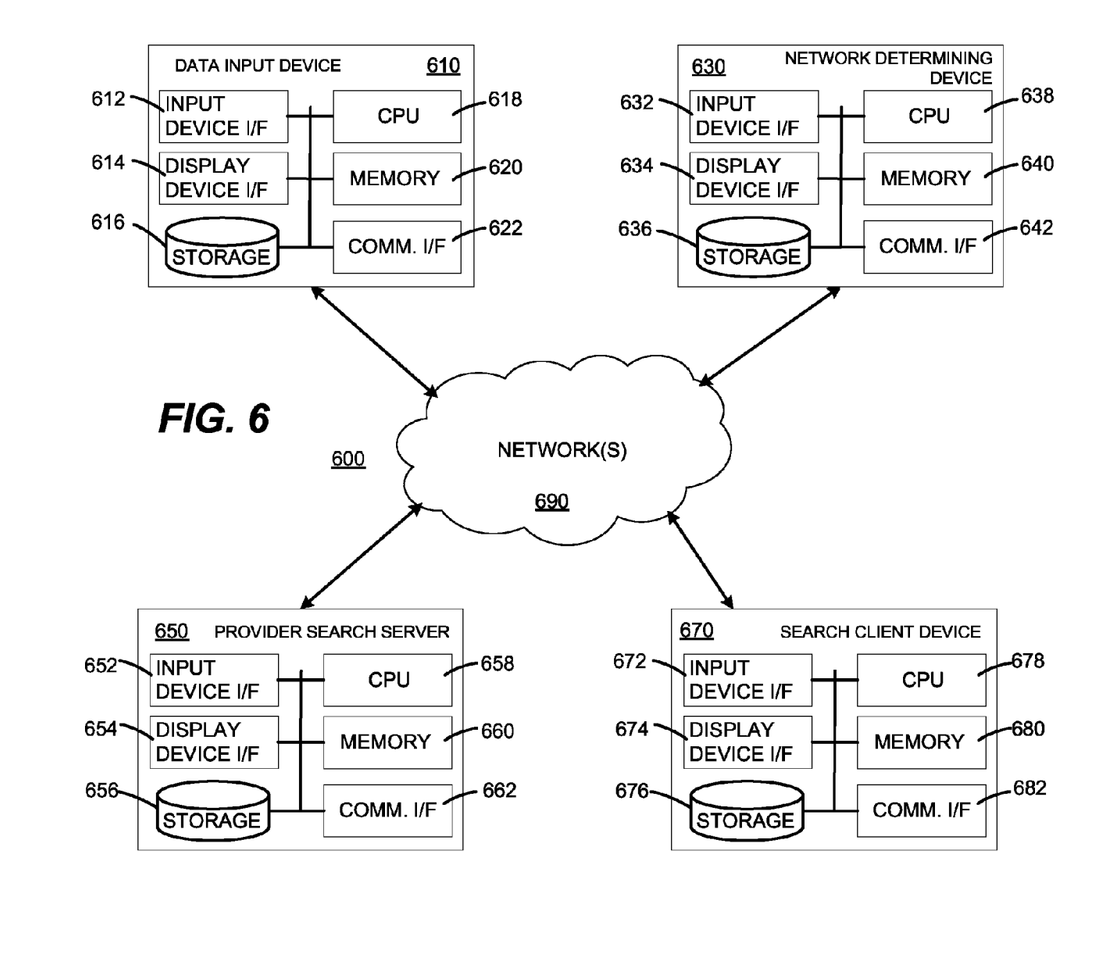
FIG. 6 shows an example system that may be used to implement the features described herein with reference to FIGS. 1-5.

FIG. 6 shows an example system 600 that may be used to implement the example architecture 100 of FIG. 1, the method 200 of FIG. 2, and/or to display the user interface element 500 of FIG. 5. The example system 600 may include a data input computer 610, a network determining computer 630, a provider search server 650, a search client device 670, and one or more communication networks 690.

The data input device 610 may include a processor 618, memory device 620, communication interface 622, input device interface 612, display device interface 614, and storage device 616. The network determining device 630 may include a processor 638, memory device 640, communication interface 642, input device interface 632, display device interface 634, and storage device 636. The provider search server 650 may include a processor 658, memory device 660, communication interface 662, input device interface 652, display device interface 654, and storage device 656. The search client device 670 may include a processor 678, memory device 680, communication interface 682, input device interface 672, display device interface 674, and storage device 676.

The data input device 610 may be configured to perform any feature or combination of features described above with reference to FIGS. 1-5 as performed by the data input module 124. The network determining device 630 may be configured to perform any feature or combination of features described above with reference to FIGS. 1-5 as performed by the claim information database module 120 and/or the network determining module 110. The provider search server 650 may be configured to perform any feature or combination of features described above with reference to FIGS. 1-5 as performed by the service provider search module 130. The search client device 670 may be configured to perform any feature or combination of features described above with reference to FIGS. 1-5 as performed by the search client module 134. The search client device 670 may be, for example, a desktop computer, a laptop computer, a netbook, a tablet computer, a personal digital assistant (PDA), a cellular phone, or any other appropriate device.

Each or any of the memory devices 620, 640, 660, 680 may be or include a device such as a Dynamic Random Access Memory (D-RAM), Static RAM (S-RAM), or other RAM or a flash memory. Each or any of the storage devices 616, 636, 656, 676 may be or include a hard disk, a magneto-optical medium, an optical medium such as a CD-ROM, a digital versatile disk (DVDs), or Blu-Ray disc (BD), or other type of device for electronic data storage.

Each or any of the communication interfaces 622, 642, 662, 682 may be, for example, a communications port, a wired transceiver, a wireless transceiver, and/or a network card. Each or any of the communication interfaces 622, 642, 662, 682 may be capable of communicating using technologies such as Ethernet, fiber optics, microwave, xDSL (Digital Subscriber Line), Wireless Local Area Network (WLAN) technology, wireless cellular technology, and/or any other appropriate technology. The communication interfaces 622, 642, 662, 682 may be used by the data input device 610, the network determining device 630, the provider search server 650, and the search client device 670 to communicate via the one or more communication networks 690. The one or more communication networks 690 may include one or more private Local Area Networks (LANs), and/or one or more public communication networks such as the Internet. The one or more communication networks 690 may be based on wired and/or wireless networking technologies.

Each or any of the input device interfaces 612, 622, 652, 672 may an interface configured to receive input from an input device such as a keyboard, a mouse, a trackball, a scanner, a touch screen, a touch pad, a stylus pad, and/or other device. Each or any of the input device interfaces 612, 622, 652, 672 may operate using a technology such as Universal Serial Bus (USB), PS/2, Bluetooth, infrared, and/or other appropriate technology.

Each or any of the display device interfaces 614, 634, 654, 674 may be an interface configured to communicate data to a display device. Each or any of the display device interfaces 614, 634, 654, 674 may operate using technology such as Video Graphics Array (VGA), Super VGA (S-VGA), Digital Visual Interface (DVI), High-Definition Multimedia Interface (HDMI), or other appropriate technology.

The memory 620 and/or the storage device 616 of the data input device 610 may store instructions which, when executed by the processor 618, cause the processor 618 to perform any feature or combination of features described above with reference to FIGS. 1-5 as performed by the data input module 124. The memory 640 and/or the storage device 636 of the network determining device 630 may store instructions which, when executed by the processor 638, cause the processor 638 to perform any feature or combination of features described above with reference to FIGS. 1-5 as performed by the claim information database module 120 and/or the network determining module 110. The memory 660 and/or the storage device 656 in the provider search server 650 may store instructions which, when executed by the processor 658, cause the processor 658 to perform any feature or combination of features described above with reference to FIGS. 1-5 as performed by the provider search server 650. The memory device 680 and/or the storage device 676 in the search client device 670 may store instructions which, when executed by the processor 678, cause the processor 678 to perform any feature or combination of features described above with reference to FIGS. 1-5 as performed by the search client module 134.

Although examples are described above in terms of workers' compensation and medical service providers, the principles described above may be applied to any other appropriate context. For example, the principles described above may be applied, mutatis mutandis, to automobile insurance, property insurance, general liability insurance, and/or any other insurance-related or non-insurance-related context.

When referred to herein, the term "display device" broadly refers to and is not limited to a monitor or television display, a plasma display, a liquid crystal display (LCD), and/or a display based on a technology such as front or rear projection, light emitting diodes (LEDs), organic light-emitting diodes (OLEDs), or Digital Light Processing (DLP).

When referred to herein, the term "computer-readable storage medium" broadly refers to and is not limited to a register, a cache memory, a ROM, a semiconductor memory device (such as a D-RAM, S-RAM, or other RAM), a magnetic medium such as a flash memory, a hard disk, a magneto-optical medium, an optical medium such as a CD-ROM, a DVDs, or BD, or other device for electronic data storage.

As used herein, the term "processor" broadly refers to and is not limited to a single- or multi-core general purpose processor, a special purpose processor, a conventional processor, a digital signal processor (DSP), a plurality of microprocessors, one or more microprocessors in association with a DSP core, a controller, a microcontroller, one or more Application Specific Integrated Circuits (ASICs), one or more Field Programmable Gate Array (FPGA) circuits, any other type of integrated circuit (IC), a system-on-a-chip (SOC), and/or a state machine.

Although features and elements are described above in particular combinations, each feature or element can be used alone or in any combination with the other features and elements. For example, each feature or element described above with reference to any one or any combination of FIGS. 1-6 may be used alone without the other features and elements or in various combinations with or without other features and elements described above with reference to any one or any combination of FIGS. 1-6. Sub-elements of the methods and features described above may be performed in any arbitrary order (including concurrently), in any combination or sub-combination.

What is claimed is:

1. A system for determining a composition of a service provider network for providing services according to a workers' compensation insurance plan, the system comprising:
   a computer-readable storage medium that stores claim information, which describes:
      workers' compensation claims; and
      medical service providers that provided medical services related to the workers' compensation claims including numerical information related to a patients' satisfaction with the medical services provided;
   at least one processor that:
      determines, for each of the medical service providers included in the stored claim information, a metric value for each of a plurality of service provider metrics based on the stored claim information, wherein the service provider metrics include:
         the information related to the patient view of the medical services provided;
         a metric that relates to an amount paid per claim; and
         a percentage of claims that involved lost time;
      adjusts the metric values based on one or more adjustment parameters;
      assigns scores to each of the medical service providers based on the adjusted metric values;
      determines an average of the assigned scores for each of the medical service providers; and
      generates results data based on the determined averages of the assigned scores, wherein the results data indicates, for each of the medical service providers, whether the medical service provider is included in the service provider network, and wherein the medical service providers with generated results below a threshold are not included in the service provider network; and
   a display device that displays the results data.

2. The system of claim 1, wherein the service provider metrics further include one or more of:
   an average number of disability days; and
   a percentage of claims that involved legal activity.

3. The system of claim 1, wherein the service provider metrics further include one or more of:
   an average claimant satisfaction;
   an average claims adjuster satisfaction; and
   an average employer satisfaction.

4. The system of claim 1, wherein the one or more adjustment parameters include:
   a type of injury associated with claims handled by the medical service provider;
   an age of claimants for claims handled by the medical service provider; and
   an age of claims handled by the medical service provider.

5. The system of claim 4, wherein the at least one processor is configured to adjust the metric values based on the one or more adjustment parameters by:
   determining an average metric value for claims with a given type of injury; and
   adjusting the metric values based on the determined average metric value.

6. The system of claim 4, wherein the at least one processor is configured to adjust the metric values based on the one or more adjustment parameters by:
   determining an average metric value for claims with claimants of a given age; and
   adjusting the metric values based on the determined average metric value.

7. The system of claim 4, wherein the at least one processor is configured to adjust the metric values based on the one or more adjustment parameters by:
   determining an average metric value for claims of a given age; and
   adjusting the metric values based on the determined average metric value.

8. The system of claim 1, wherein the at least one processor is further configured to determine whether,
   for each of the medical service providers, the medical service provider is included in the service provider network or not based on
   whether the average of the assigned scores for the medical service provider is above or below a threshold value.

9. The system of claim 1, further comprising:
   at least one communication interface, configured to receive one or more search parameters that indicate a search for a medical service provider to obtain medical services;
   wherein the at least one processor is configured to generate search response information, wherein the search response information includes information related to medical service providers that are included in the service provider network, and does not include information related to medical service providers that are not included in the service provider network; and wherein the at least one communication interface is further configured to transmit the search response information.

10. The system of claim 1, wherein the at least one processor is configured to assign the scores to each of the medical service providers based on percentage ranges for each of the service provider metrics and scores that correspond to each of the percentage ranges, wherein the percentage ranges and corresponding scores include:

a percentage range of ninety percent to one hundred percent, which corresponds to a score of five;

a percentage range of seventy-five percent to ninety percent, which corresponds to a score of four;

a percentage range of fifty percent to seventy-five percent, which corresponds to a score of three;

a percentage range of twenty-five percent to fifty percent, which corresponds to a score of two;

a percentage range of ten percent to twenty-five, which corresponds to a score of one; and a percentage range of zero percent to ten percent, which corresponds to a score of zero.

11. A computer-implemented method for determining a composition of a service provider network, the method comprising:

a computer-readable storage medium storing claim information, wherein the claim information describes:

workers' compensation claims; and medical service providers that provided medical services related to the workers' compensation claims including numerical information related to patients' satisfaction with the medical services provided;

at least one processor determining, for each of the medical service providers, a metric value for each of a plurality of service provider metrics based on the claim information, wherein the service provider metrics include:

the information related to the patient view of the medical services provided;

a metric that relates to an amount paid per claim; and a percentage of claims that involved lost time;

the at least one processor adjusting the metric values based on one or more adjustment parameters;

the at least one processor assigning scores to each of the medical service providers based on the adjusted metric values;

the at least one processor determining averages of the assigned scores for each of the medical service providers; and the at least one processor generating results data based on the determined averages of the assigned scores, wherein the results data indicates, for each of the medical service providers, whether the medical service provider is included in the service provider network, and wherein the medical service providers with generated results below a threshold are not included in the service provider network; and a display device displaying the results data.

12. The method of claim 11, wherein the service provider metrics further include one or more of:

an average number of disability days; and a percentage of claims that involved legal activity.

13. The method of claim 11, wherein the service provider metrics further include one or more of:

an average claimant satisfaction;

an average claims adjuster satisfaction; and an average employer satisfaction.

14. The method of claim 11, wherein the one or more adjustment parameters include:

a type of injury associated with claims handled by the medical service provider;

an age of claimants for claims handled by the medical service provider; and an age of claims handled by the medical service provider.

15. The method of claim 14, wherein the adjusting the metric values based on the one or more adjustment parameters includes:

determining an average metric value for claims with a given type of injury; and adjusting the metric values based on the determined average metric value.

16. The method of claim 14, wherein the adjusting the metric values based on the one or more adjustment parameters includes:

determining an average metric value for claims with claimants of a given age; and adjusting the metric values based on the determined average metric value.

17. The method of claim 14, wherein the adjusting the metric values based on the one or more adjustment parameters includes:

determining an average metric value for claims of a given age; and adjusting the metric values based on the determined average metric value.

18. The method of claim 11, further comprising:

the at least one processor determining whether, for each of the medical service providers, the medical service provider is included in the service provider network or not based on whether the average of the assigned scores for the medical service provider is above or below a threshold value.

19. The method of claim 11, further comprising:

at least one communication interface receiving one or more search parameters that indicate a search for a medical service provider to obtain medical services;

the at least one processor generating search response information, wherein the search response information includes information related to medical service providers that are included in the service provider network, and does not include information related to medical service providers that are not included in the service provider network; and the at least one communication interface transmitting the search response information.

20. The method of claim 11, wherein the assigning the scores to each of the service providers is performed based on percentage ranges for each of the service provider metrics and scores that correspond to each of the percentage ranges, wherein the percentage ranges and corresponding scores include:

a percentage range of ninety percent to one hundred percent, which corresponds to a score of five;

a percentage range of seventy-five percent to ninety percent, which corresponds to a score of four;

a percentage range of fifty percent to seventy-five percent, which corresponds to a score of three;

a percentage range of twenty-five percent to fifty percent, which corresponds to a score of two;

a percentage range of ten percent to twenty-five, which corresponds to a score of one; and a percentage range of zero percent to ten percent, which corresponds to a score of zero.

21. A computer-readable medium having processor-executable instructions stored thereon which, when executed by at least one processor, will cause the at least one processor to perform a method for determining a composition of a service provider network, the method comprising:

receiving claim information, wherein the claim information describes:
workers' compensation claims; and
medical service providers that provided medical services related to the workers' compensation claims including numerical information related to at least one of a patients' satisfaction with the medical services provided;

determining, for each of the medical service providers, a metric value for each of a plurality of service provider metrics based on the claim information, wherein the service provider metrics include:
the information related to the patient view of the medical services provided;
a metric that relates to an amount paid per claim; and
a percentage of claims that involved lost time;

adjusting the metric values based on one or more adjustment parameters;

assigning scores to each of the medical service providers based on the adjusted metric values;

determining averages of the assigned scores for each of the medical service providers; and generating results data based on the determined averages of the assigned scores, wherein the results data indicates, for each of the medical service providers, whether the medical service provider is included in the service provider network, and wherein the medical service providers with generated results below a threshold are not included in the service provider network; and displaying the results data via a display device.

22. The computer-readable medium of claim 21, wherein the service provider metrics further include one or more of:
an average number of disability days; and
a percentage of claims that involved legal activity.

23. The computer-readable medium of claim 21, wherein the service provider metrics further include one or more of:
an average claimant satisfaction;
an average claims adjuster satisfaction; and
an average employer satisfaction.

24. The computer-readable medium of claim 21, wherein the one or more adjustment parameters include:
a type of injury associated with claims handled by the medical service provider;
an age of claimants for claims handled by the medical service provider; and
an age of claims handled by the medical service provider.

25. The computer-readable medium of claim 24, wherein the adjusting the metric values based on the one or more adjustment parameters includes:
determining an average metric value for claims with a given type of injury; and
adjusting the metric values based on the determined average metric value.

26. The computer-readable medium of claim 24, wherein the adjusting the metric values based on the one or more adjustment parameters includes:
determining an average metric value for claims with claimants of a given age; and
adjusting the metric values based on the determined average metric value.

27. The computer-readable medium of claim 24, wherein the adjusting the metric values based on the one or more adjustment parameters includes:
determining an average metric value for claims of a given age; and
adjusting the metric values based on the determined average metric value.

28. The computer-readable medium of claim 21, wherein the method further comprises:
determining whether, for each of the medical service providers, the medical service provider is included in the service provider network or not based on whether the average of the assigned scores for the medical service provider is above or below a threshold value.

29. The computer-readable medium of claim 21, wherein the method further comprises:
receiving one or more search parameters that indicate a search for a medical service provider to obtain medical services via at least one communication interface;
generating search response information, wherein the search response information
includes information related to medical service providers that are included in the service provider network, and
does not include information related to medical service providers that are not included in the service provider network; and
transmitting the search response information via the at least one communication interface.

30. The computer-readable medium of claim 21, wherein the assigning the scores to each of the service providers is performed based on percentage ranges for each of the service provider metrics and scores that correspond to each of the percentage ranges, wherein the percentage ranges and corresponding scores include:
a percentage range of ninety percent to one hundred percent, which corresponds to a score of five;
a percentage range of seventy-five percent to ninety percent, which corresponds to a score of four;
a percentage range of fifty percent to seventy-five percent, which corresponds to a score of three;
a percentage range of twenty-five percent to fifty percent, which corresponds to a score of two;
a percentage range of ten percent to twenty-five, which corresponds to a score of one; and
a percentage range of zero percent to ten percent, which corresponds to a score of zero.

* * * * *